United States Patent [19]
Hahnen

[11] Patent Number: 6,033,420
[45] Date of Patent: Mar. 7, 2000

[54] TROCAR INTRODUCER SYSTEM AND METHODS OF USE

[75] Inventor: Kevin Hahnen, San Jose, Calif.

[73] Assignee: Embol-X, Inc., Mountain View, Calif.

[21] Appl. No.: 09/146,216

[22] Filed: Sep. 2, 1998

[51] Int. Cl.⁷ .................................................. A61B 17/34
[52] U.S. Cl. ............................................ 606/185; 128/898
[58] Field of Search ................................ 606/185, 167, 606/170; 604/158, 164; 128/898

[56] References Cited

U.S. PATENT DOCUMENTS

| | | | |
|---|---|---|---|
| 5,445,645 | 8/1995 | Debbas | 606/185 |
| 5,490,843 | 2/1996 | Hildwein et al. | 604/264 |
| 5,924,424 | 7/1999 | Stevens et al. | 606/185 |

*Primary Examiner*—Michael Buiz
*Assistant Examiner*—Kevin Truong
*Attorney, Agent, or Firm*—Lyon & Lyon LLP

[57] ABSTRACT

A trocar introducer system having a trocar slideably inserted into a lumen of a cannula. The trocar has an elongate member which comprises a proximal end and a distal end. An actuating mechanism is mounted at the proximal end of the trocar and operates a surgical blade which is mounted on the distal end of the trocar. The cannula may have a suture flange, drainage ports, a balloon occluder, and/or threads to facilitate delivery of medical therapies to a body tissue. Methods of using the devices herein are also disclosed.

7 Claims, 11 Drawing Sheets

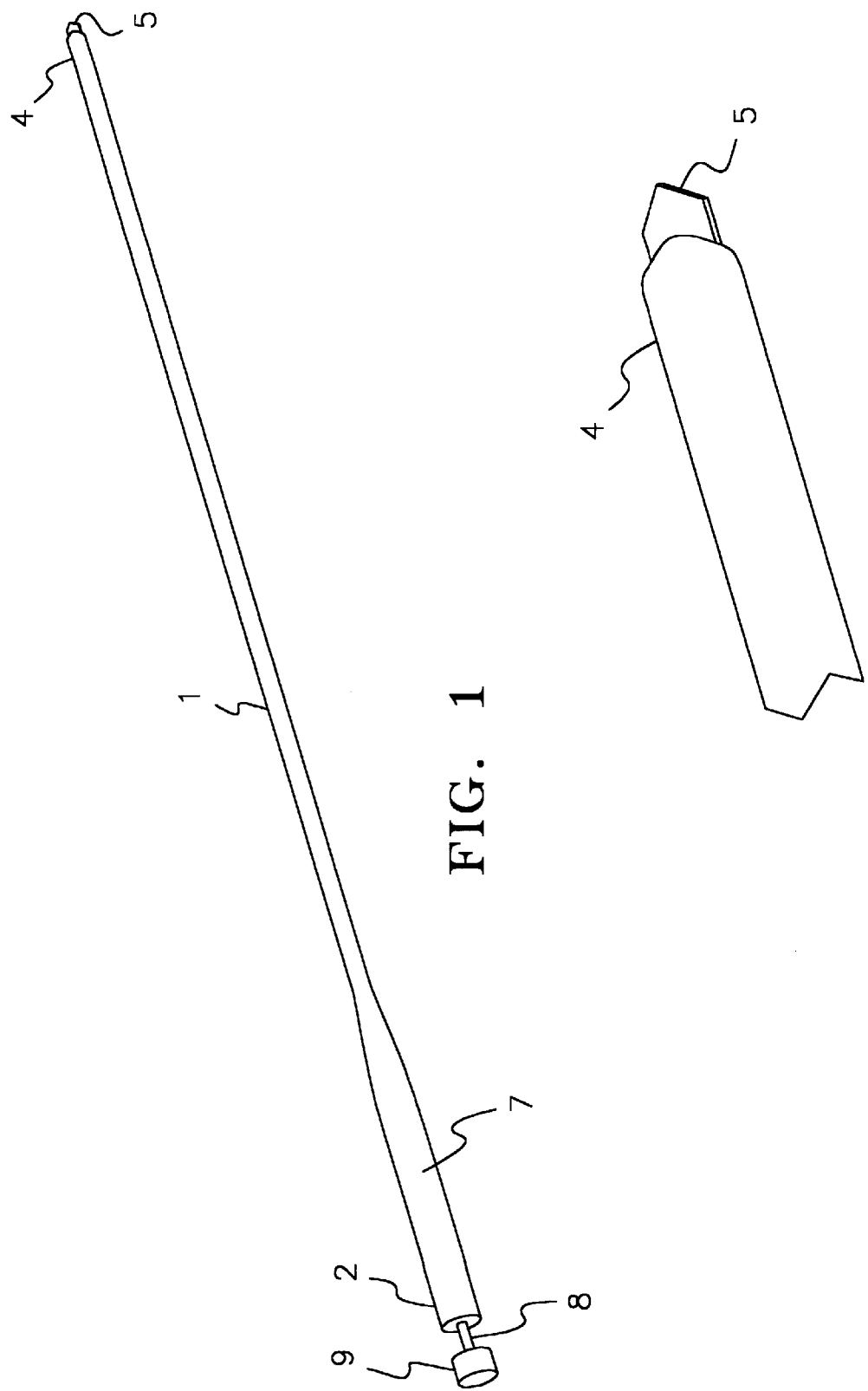

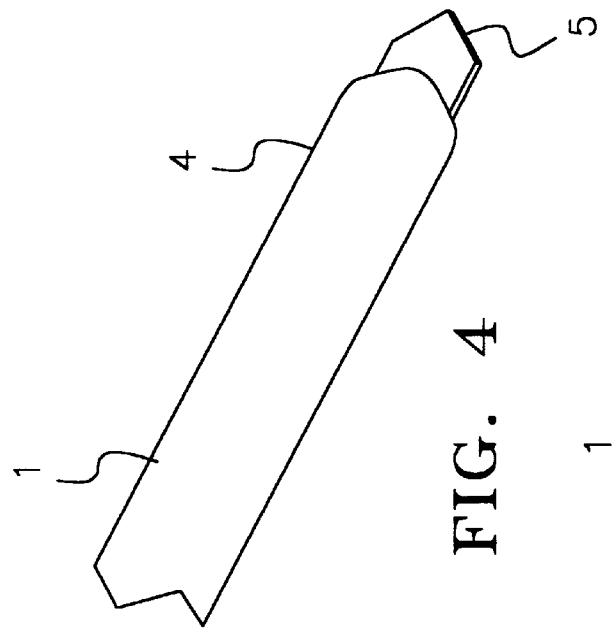
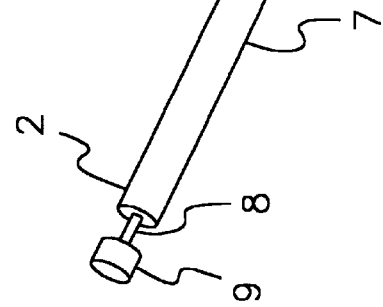
FIG. 4
FIG. 3

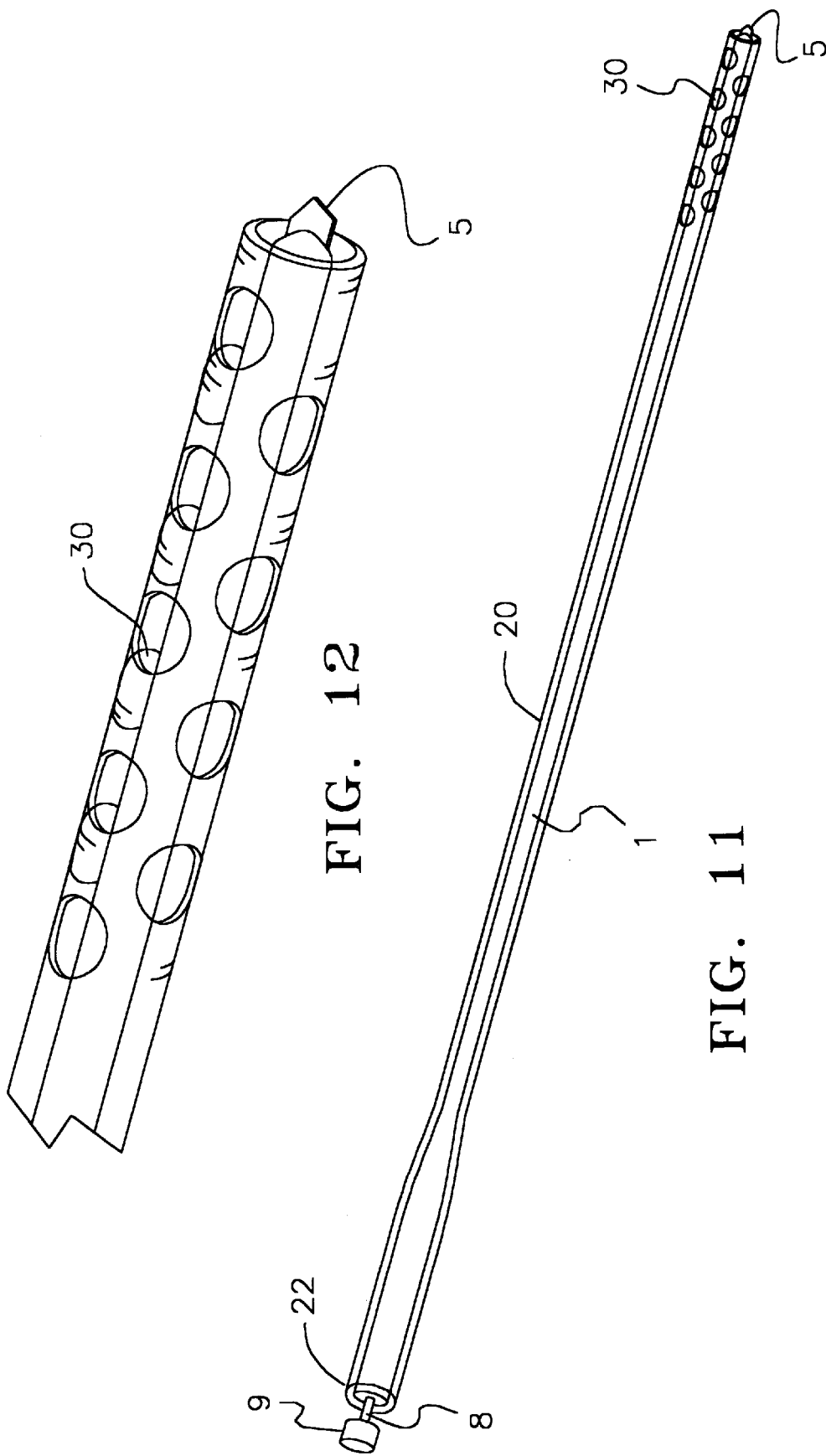

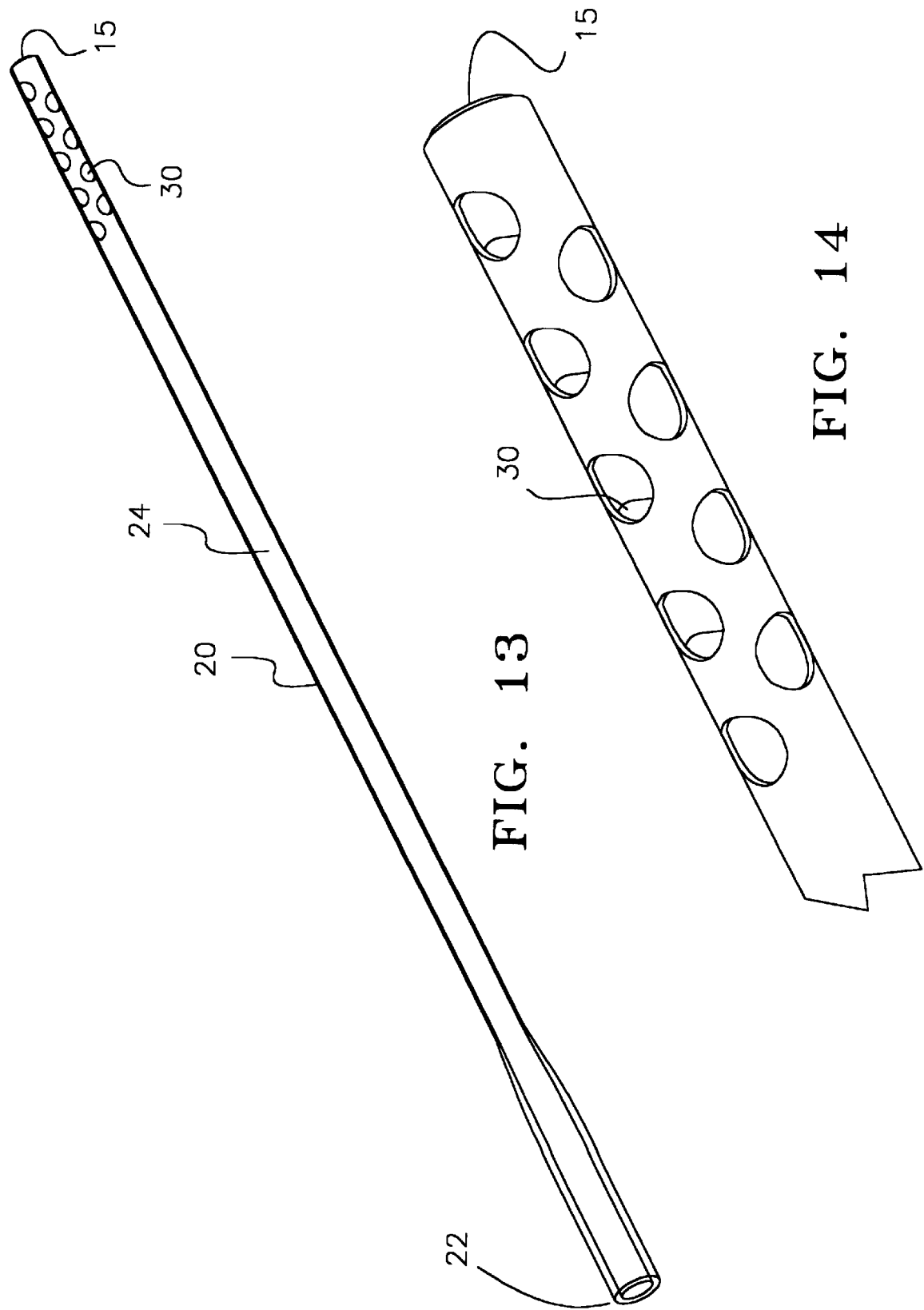

TROCAR INTRODUCER SYSTEM AND METHODS OF USE

FIELD OF THE INVENTION

The present invention relates generally to a trocar introducer system which provides access to a body tissue, including a patient's vascular system, and serves as a conduit to apply other medical therapies, such as delivery of oxygenated blood.

BACKGROUND OF THE INVENTION

Myocardial infarction is one of the most common diagnosis occurring in hospitalized patients in Western countries. In the United States, approximately 1.5 million myocardial infarctions occur each year. Myocardial infarction generally occurs with abrupt decrease in coronary blood flow that follows a thrombotic occlusion of a coronary artery previously narrowed by atherosclerosis. Once severe stenosis of a coronary artery has reduced the cross-sectional area by more than approximately seventy percent, a patient is likely to develop clinical manifestation of coronary artery disease, which includes angina pectoris, myocardial infarction, ventricular arrhythmia, and sudden death. Therefore, in patients with severe coronary artery disease, aggressive medical therapy and mechanical revascularization, including percutaneous transluminal coronary angioplasty, coronary atherectomy, coronary stent placement, and coronary artery bypass grafting surgery, are often indicated to improve a patient's quality of life and survival.

Excellent long-term results have been obtained with conventional coronary artery bypass grafting surgery. However, significant mortality and morbidity still exist due to the use of cardiopulmonary bypass for circulatory support and the traditional method of access by median sternotomy. To alleviate these problems, an endovascular or port-access technique for cardiopulmonary bypass and cardioplegic arrest has been developed for use in cardiac surgery. This peripherally based system achieves aortic occlusion, cardioplegia delivery, and left ventricular decompression. Thus, coronary revascularization and various cardiac procedures, which include valvular repair, septal defect repair, atherectomy, aneurysm repair, and correction of congenital defects, can be effectively performed in a less invasive fashion.

Traditionally, multiple cannulation sites are required for placement of arterial and venous return cannulas for cardiopulmonary bypass. Moreover, an additional access mechanism is generally required for insertion of these cannulas. Problems associated with these techniques are that they may increase a patient's surgical morbidity. A need therefore exists for minimally invasive devices and methods which facilitate delivery of medical therapy and provide an access mechanism for cannulation of body tissues.

SUMMARY OF THE INVENTION

The invention provides less-invasive devices and methods for cannulating a body tissue or body cavity and infusing a fluid herein. More particularly, the invention provides a trocar introducer system which includes an access mechanism for insertion of cannulas. The methods and devices of the invention eliminate the need for a median sternotomy or thoracotomy to obtain access into thoracic cavity. The present invention is therefore useful when peripheral vascular access is unavailable due to inadequate vessel diameter, vessel stenosis, vascular injury or other conditions.

In a preferred embodiment, the trocar introducer system makes use of a cannula which comprises a proximal end, a distal end, and a lumen therebetween. A rigid trocar, which comprises an elongate member having a proximal end and a distal end, is slideably inserted into the lumen of the cannula. The elongate member has an actuating mechanism mounted on its proximal end and a surgical blade mounted on its distal end. The surgical blade is operable by manipulating the actuating mechanism.

In another embodiment, the rigid trocar has a handle mounted on the proximal end of the elongate member. The handle may be distal the actuating mechanism, and facilitates operation of the actuating mechanism.

In another embodiment, the actuating mechanism includes a shaft carried by a lumen of the trocar. The shaft is connected at its distal end to the surgical blade. The shaft may have a knob at its proximal end and may operate against the force of a spring. In certain embodiments, the surgical blade may have a protecting sleeve.

The rigid trocar can be inserted into the lumen of a variety of cannulas to provide vascular access in minimally invasive procedures. In one embodiment, the cannula may include venous drainage ports and a lumen adapted for drainage of deoxygenated blood from the right atrium to a bypass oxygenator machine. In another embodiment, a balloon occluder is mounted at the distal end of the cannula to provide aortic occlusion for circulatory isolation of the heart and coronary blood vessels from the peripheral vascular system. In still another embodiment, the cannula has threads at its distal end to provide better stabilization between the cannula and the body tissue.

The methods of present invention relate to cannulation of a body tissue, including a patient's blood vessel, using the trocar introducer system described above. The rigid trocar, which comprises an elongate member having a proximal end and a distal end, is inserted in the lumen of a cannula. In minimally invasive procedures, an incision on a patient's intercostal space is made for access into the thoracic cavity, thereby reducing trauma to the chest wall as compared to the traditional open chest approach. The distal end of the cannula is inserted through the chest wall incision. During aortic cannulation, for example, an incision on the aorta is made by the surgical blade mounted on the distal end of the trocar. The cannula is then introduced through the incision and advanced distally into the aorta. After placement of the cannula, the elongate member is withdrawn from the lumen of the cannula. The lumen of the cannula is now available for delivery of oxygenated blood from a bypass oxygenator machine or for delivery of cardioplegia solution to the heart to arrest heart function. After cardiac arrest is achieved and cardiopulmonary bypass is initiated for circulatory support, a variety of cardiothoracic surgeries, including coronary artery bypass grafting, valvular repair and replacement, septal defect repair, aneurysm repair, removal of atrial myxoma, and correction of congenital defects, can then be performed.

It will be understood that there are many advantages to using a trocar introducer system as disclosed herein. For example, the trocar introducer system provides an access mechanism for cannulation of a body tissue, thereby obviating the need for an additional access device. In addition, the trocar introducer system can be employed in various minimally invasive surgeries. Moreover, the trocar introducer system can be utilized to deliver fluid and blood to a body tissue, and to apply other medical therapy such as aspirators, filters, pressure monitors, atherectomy devices, and dilatation catheters.

BRIEF DESCRIPTION OF THE DRAWINGS

FIG. 1 depicts a rigid trocar according to a first embodiment.

FIG. 2 depicts a distal end of the trocar shown in FIG. 1.

FIG. 3 depicts a rigid trocar according to another embodiment having a longer trocar.

FIG. 4 depicts a distal end of the trocar shown in FIG. 2.

FIG. 11 depicts a trocar introducer system according to another embodiment in which the cannula has drainage ports.

FIG. 12 depicts a distal end of the trocar introducer system shown in FIG. 11.

FIG. 13 depicts another embodiment of a cannula having venous drainage ports.

FIG. 14 depicts a distal end of the cannula shown in FIG. 13.

DETAILED DESCRIPTION

Figure 5:
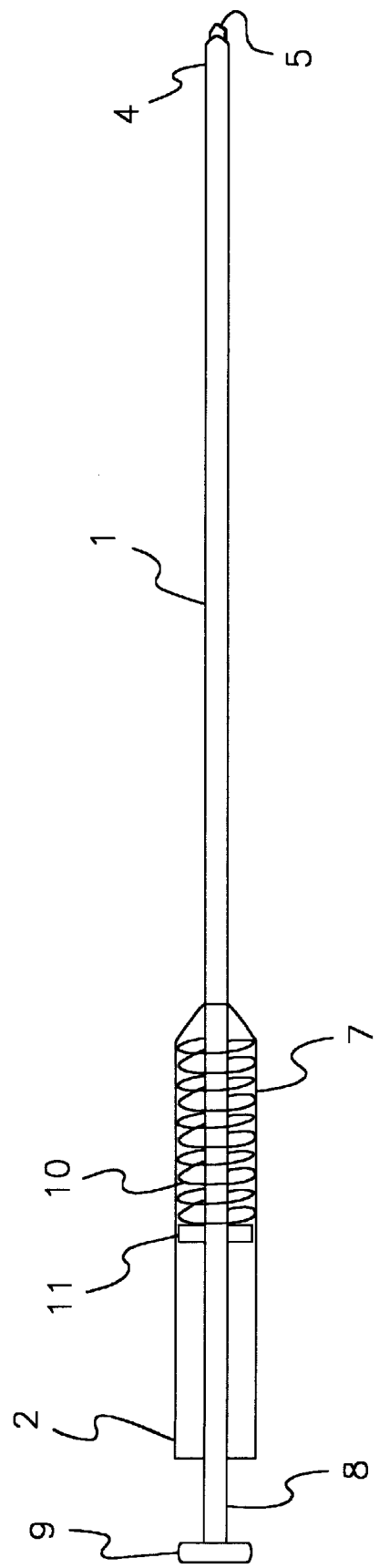
FIG. 5 depicts a rigid trocar according to another embodiment having a spring in a handle.

The devices and methods of the invention facilitate delivery of medical therapy to a body tissue and cannulation of the body tissue by providing an access mechanism. Although the invention works best in minimally invasive cardiothoracic surgeries, it will be understood that the devices and methods disclosed herein can also be utilized in open chest procedures.

FIG. 1 and FIG. 2 depict a trocar according to a first embodiment. The trocar has elongate member 1, proximal end 2, and distal end 4. Surgical blade 5 is mounted on distal end 4, and is operable by manipulating an actuating mechanism at the proximal end of the trocar. Shaft 8 connects surgical blade 5 at the distal end, and knob 9 at the proximal end of the trocar. Handle 7 at the proximal end of the trocar facilitates operation of the surgical blade. In use, knob 9 is pushed distally against handle 7 to advance shaft 8 distally in order to expose surgical blade 5 for incising a body tissue. FIG. 2 depicts a detailed view of surgical blade 5 mounted at distal end 4 of the trocar.

FIG. 3 and FIG. 4 depict a trocar according to another embodiment. Similar to the trocar depicted in FIG. 1, the trocar in FIG. 3 has elongate member 1, proximal end 2, and distal end 4. Proximal end 2 has knob 9, shaft 8, and handle 7 for activating surgical blade 5 mounted at distal end 4. The length of elongate member 1 in this trocar is longer than that of the trocar depicted in FIG. 1. A longer trocar is needed to fit within the lumen of a long cannula for incising, for example, an aorta in patients who may have excessive body fat between the chest wall and the great vessels.

FIG. 5 depicts a trocar according to another embodiment having spring 10 contained in handle 7. Again shaft 8 connects to knob 9 at proximal end 2 and surgical blade 5 at distal end 4 of the trocar. In use, surgical blade 5 is advanced distally by pushing knob 9 against handle 7, thereby operating shaft 8 against the force of spring 10. After a body tissue is incised by the surgical blade, knob 9 is released from handle 7 and spring 10 uncoils against stopper 11 to withdraw the surgical blade from the body tissue.

Figure 7:
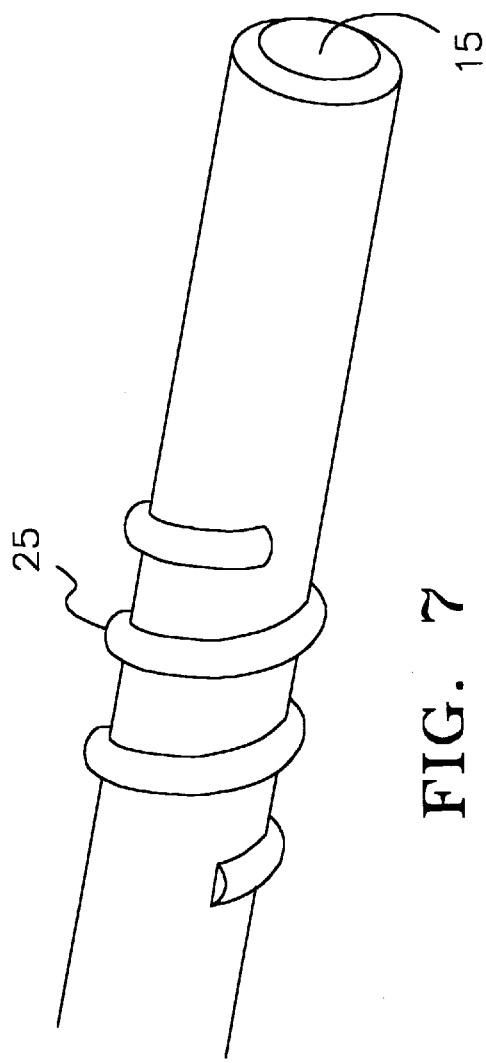
FIG. 7 depicts a distal end of the cannula shown in FIG. 6.
Figure 6:
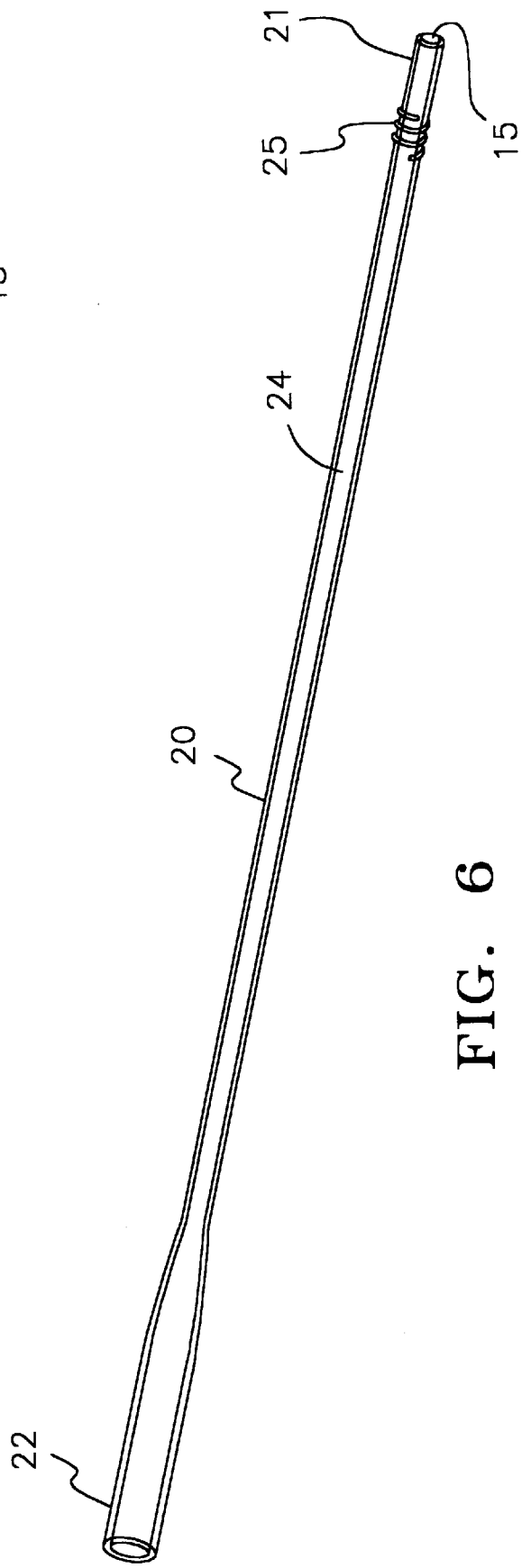
FIG. 6 depicts an embodiment of a cannula having a helical thread.

The trocar introducer system can be used with a variety of cannulas mentioned above. One embodiment of the cannula is shown in FIG. 6 and FIG. 7. Cannula 20 has proximal end 22, distal end 21, and lumen 24 therebetween. Helical thread 25 is disposed about distal end 21 of the cannula, the thread providing better contact and therefore stabilization between the cannula and a body tissue. FIG. 7 depicts a detailed view of distal end 4 of the cannula. Fluid, blood, or surgical instruments can be delivered to a body tissue through lumen 24 and port 15 of the cannula.

Figure 8:
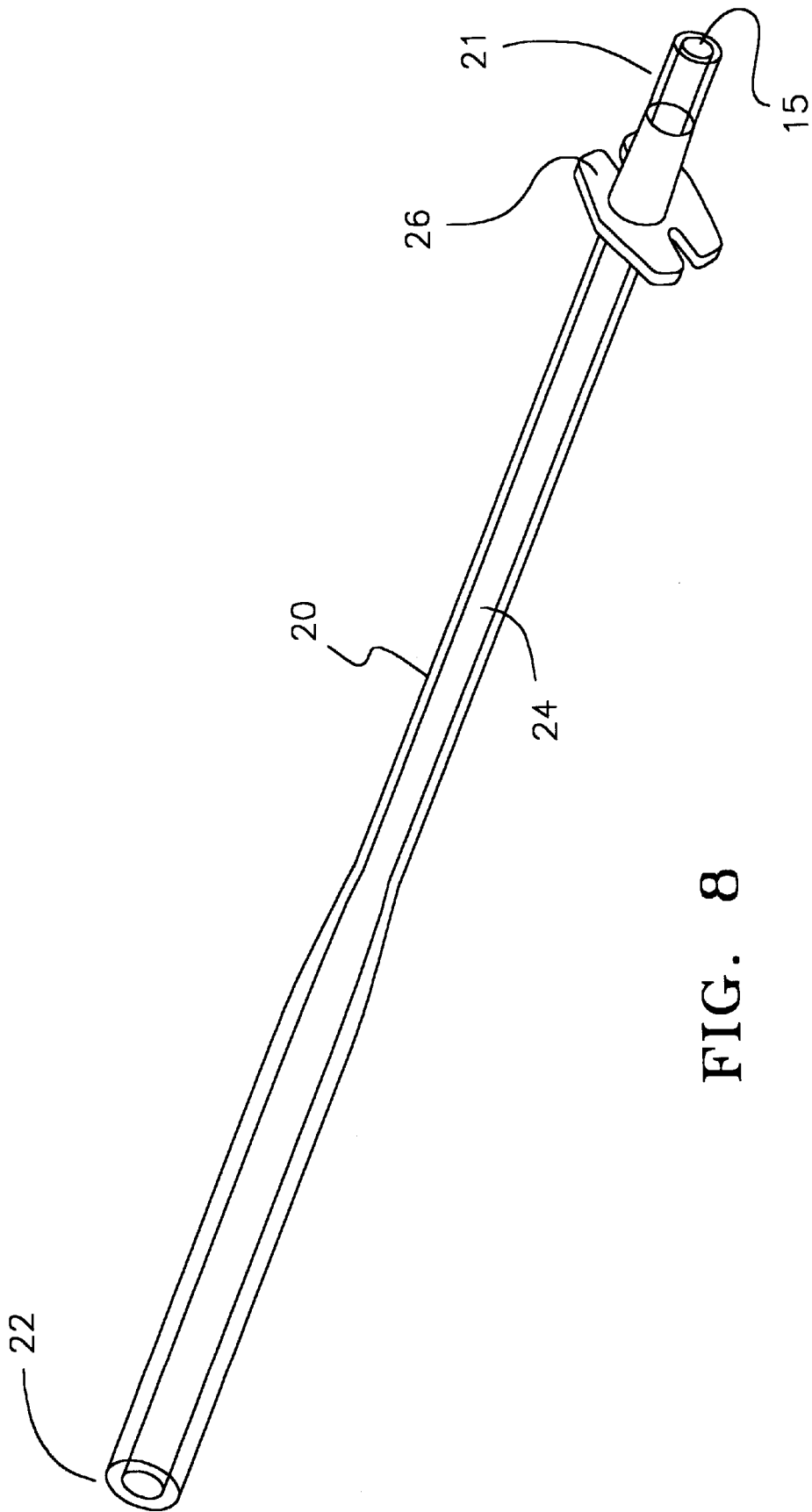
FIG. 8 depicts another embodiment of a cannula having a suture flange.
Figure 9:
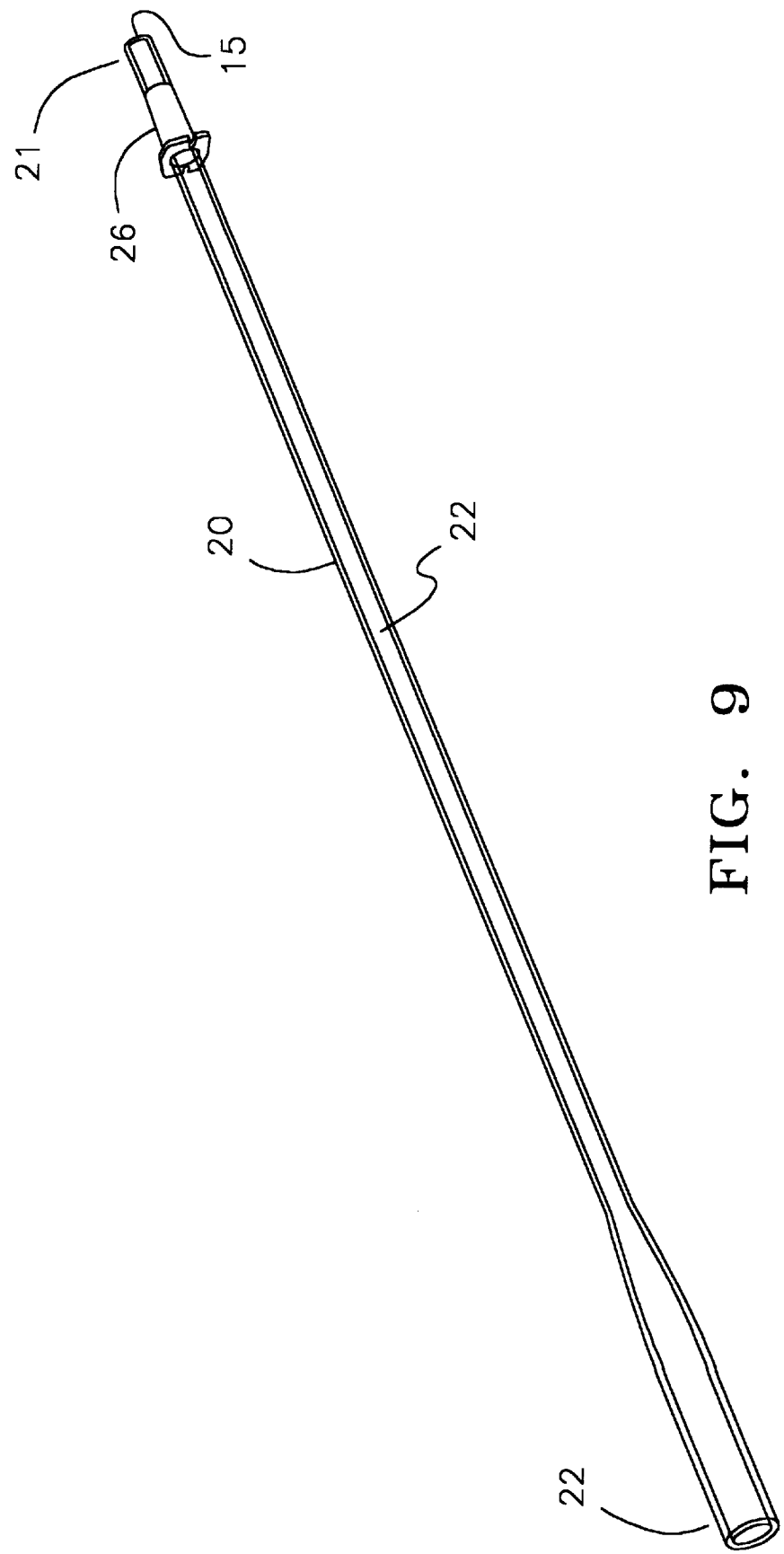
FIG. 9 depicts another embodiment of a cannula having a slideable suture flange.
Figure 10:
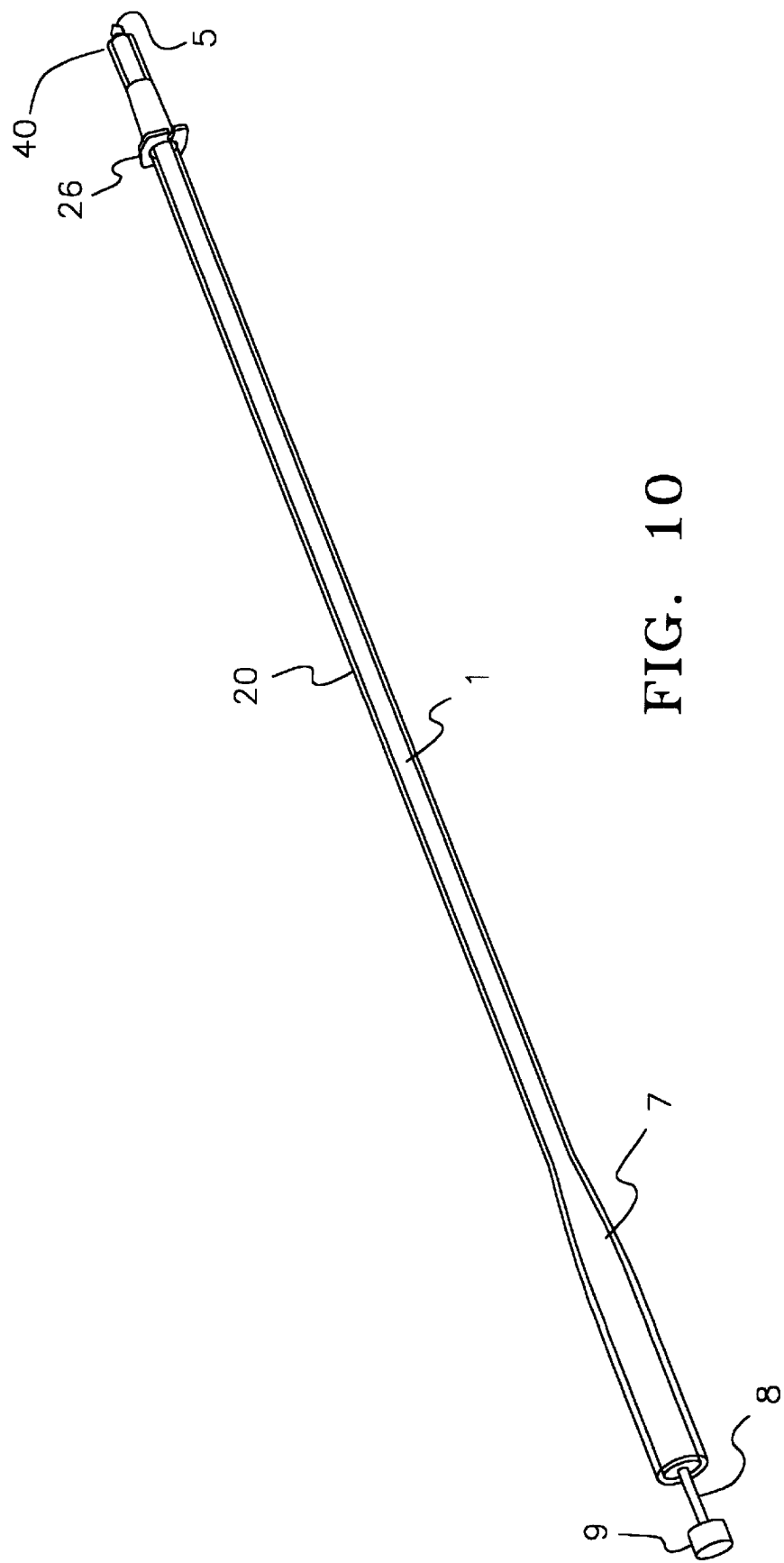
FIG. 10 depicts a trocar introducer system utilizing the cannula shown in FIG. 9.

FIG. 8, FIG. 9, and FIG. 10 depict another embodiment of a cannula having a suture flange mounted at distal end 21. Suture flange 26 is adapted for holding surgical sutures to secure the cannula onto a body tissue. This cannula may be useful for delivery of oxygenated blood through lumen 24 and port 15 to an aorta from a bypass oxygenator machine. Proximal end 22 of the cannula may be shaped for attachment to a bypass oxygenator machine. Suture flange 26 may be slideable on distal end 21 of the cannula as shown in FIG. 9 so that the length of the cannula inserted inside a body tissue is adjustable. The cannula of FIG. 9 is equipped with a longer lumen 24 than the cannula in FIG. 8.

FIG. 10 depicts a trocar introducer system in which a rigid trocar having elongate member 1 is inserted in a lumen of cannula 20. In use, the proximal end of the trocar has knob 9 and shaft 8 which, upon activation, will advance surgical blade 5 at the distal end of the trocar to incise a body tissue, thereby providing access for cannula 20. After the distal end of the cannula is inserted into a body tissue, sutures can be placed between suture flange 26 and the body tissue to secure the cannula. The trocar is then withdrawn from the lumen of the cannula, thereby leaving the lumen available to enable medical therapies. Moreover, since the suture flange is slideable at the distal end of the cannula, distal region 40 of the cannula (inserted inside a body tissue) can easily be adjusted to accommodate changing surgical conditions or medical therapy.

FIG. 11 and FIG. 12 depict a trocar introducer system according to another embodiment in which cannula 20 has drainage ports 30 at its distal end. In FIG. 11, the trocar having elongate member 1 is shown positioned within a lumen of cannula 20. The proximal end of the trocar again has knob 9 and shaft 8 which connects to surgical blade 5 at the distal end of the trocar. When knob 9 is pushed distally, surgical blade 5 will advance distally to incise a body tissue to provide access for insertion of cannula 20. Proximal end 22 of the cannula is also adapted for attachment to a bypass oxygenator machine.

A detailed view of the distal end of the trocar introducer system is depicted in FIG. 12. This embodiment of the trocar introducer system can be used to provide drainage of deoxygenated blood from the right atrium to a bypass oxygenator machine. In use, the right atrium is incised by surgical blade 5 upon manipulating the actuating mechanism at the proximal end of the trocar. The distal end of the cannula is then advanced into the right atrium and the trocar is removed from the lumen of the cannula. Proximal end 22 of the cannula is connected by an attachment to a bypass oxygenator machine, and deoxygenated blood can then be drained from the right atrium through drainage ports 30 to the bypass oxygenator machine.

FIG. 13 and FIG. 14 depict another embodiment of a venous drainage cannula. A plurality of venous drainage ports 30 are located at the distal end of cannula 20 and communicate with lumen 24 of the cannula. Proximal end 22 is adapted for attachment to a bypass oxygenator machine. When the cannula is inserted into the right atrium, inferior vena cava, or superior vena cava, venous blood is delivered from drainage ports 30 and lumen 24 to a bypass oxygenator machine.

Figure 15:
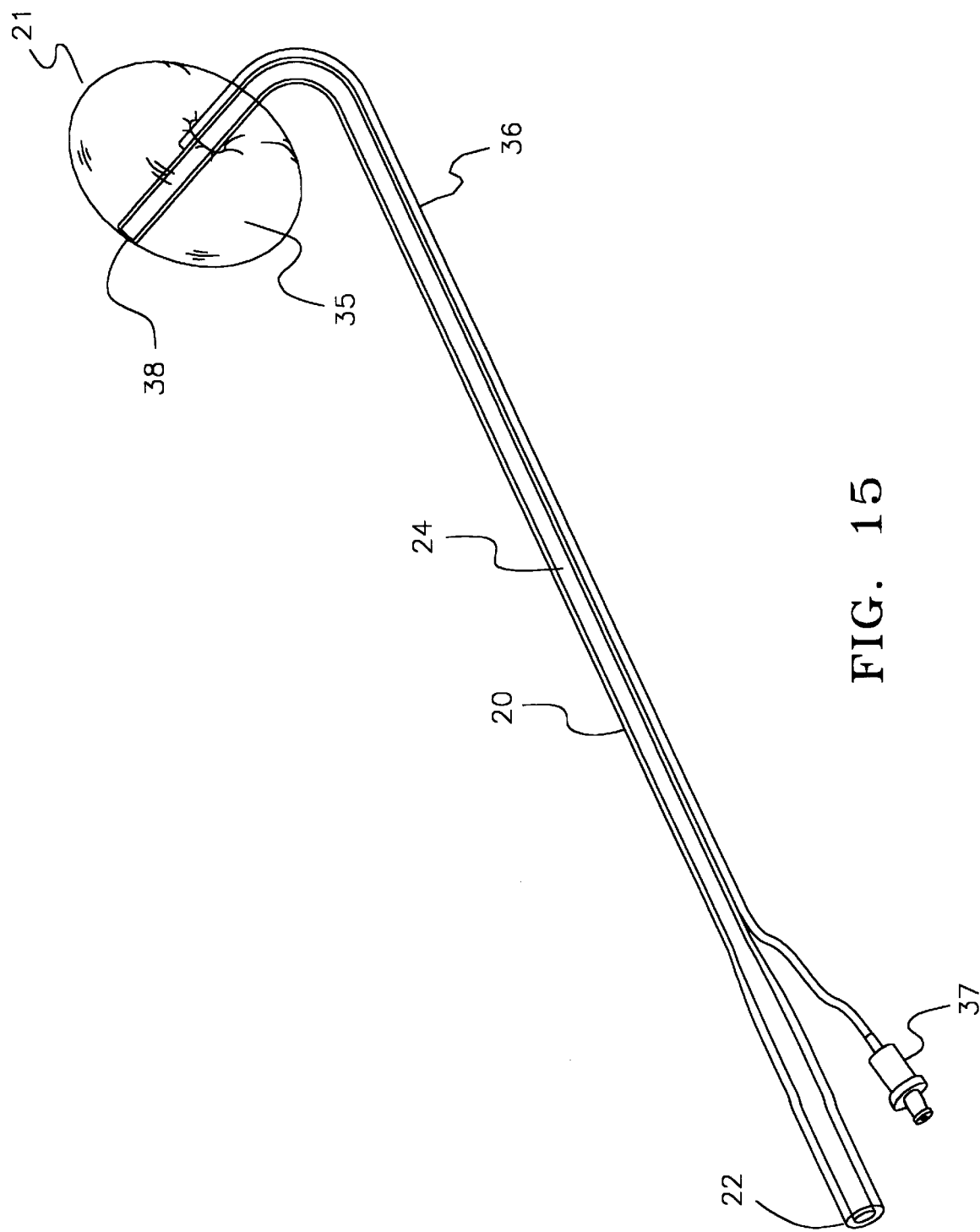
FIG. 15 depicts another embodiment of a cannula having a balloon occluder.

FIG. 15 depicts another embodiment of a cannula having balloon occluder 35 mounted at distal end 21 of the cannula and communicating with inflation lumen 36 and inflation port 37. Distal end 21 is angulated relative to proximal end 22 of the cannula. The cannula can be utilized to provide aortic occlusion for circulatory isolation of the heart and coronary blood vessels from the peripheral vascular system through inflating balloon occluder 35, and to deliver oxygenated blood from a bypass oxygenator machine through lumen 24 and port 38. Proximal end 22 is adapted for attachment to a bypass oxygenator machine.

Figure 16:
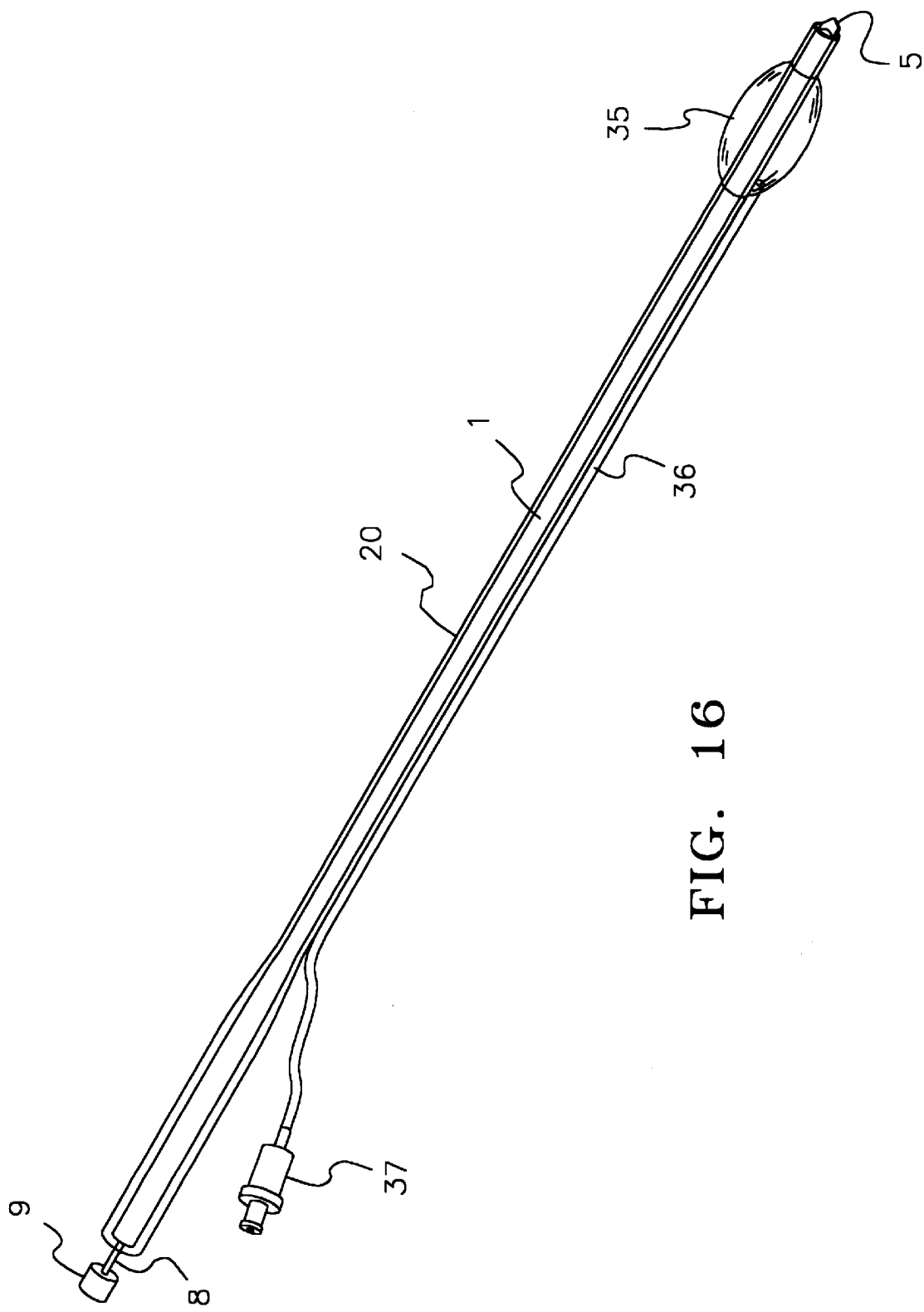
FIG. 16 depicts a rigid trocar inserted in the lumen of the cannula shown in FIG. 15.

FIG. 16 depicts a trocar introducer system utilizing the cannula shown in FIG. 15. The distal end of the cannula, which can be flexible, has a linear configuration relative to the proximal end when the trocar is inserted in the lumen of the cannula. The trocar provides access for cannulation of the aorta by surgical blade 5 at the proximal end of the trocar, comprising knob 9 and shaft 8. After the aorta is incised and the cannula is inserted into the aorta, the trocar is removed from the lumen of the cannula, thereby allowing the distal end of the cannula to regain its preformed angulated configuration as depicted in FIG. 15. A significant feature of using the trocar introducer system here is that the cannula can be more easily inserted in the aorta in a linear configuration than an angulated configuration. The balloon occluder can then be inflated to provide aortic occlusion, and the lumen of the cannula is available to deliver oxygenated blood from a bypass oxygenator machine to the aorta.

The length of the elongate member of the trocar is generally between 3 and 20 inches, preferably approximately 5 inches and 12 inches in a short and long trocar as depicted in FIG. 1 and FIG. 3, respectively. The length of the handle, which comprises a slope joining the handle and the elongate member, is generally between 0.8 and 2 inches, preferably approximately 1.5 inches. The outer diameter of the elongate member is generally between 0.1 and 0.3 inches, preferably approximately 0.17 inches. When an actuating mechanism is activated at the proximal end of the trocar, the surgical blade is exposed distally at preferably approximately no more than 3 millimeters. The length of the cannula is generally between 6 and 25 inches, preferably approximately 16.5 inches. The length of the proximal end of the cannula which accommodates the handle of the trocar is generally between 2 and 6 inches, preferably approximately 4.5 inches. The length of the cannula which accommodates the slope of the trocar is generally between 0.8 and 2 inches, preferably approximately 1.5 inches. The outer diameter of the proximal end of the cannula is generally between 0.3 and 0.7 inches, preferably approximately 0.55 inches. The inner diameter of the proximal end of the cannula is generally between 0.2 and 0.6 inches, preferably approximately 0.37 inches. The outer diameter of the distal end of the cannula is generally between 0.1 and 0.4 inches, preferably approximately 0.26 inches. The inner diameter of the distal end of the cannula is generally between 0.08 and 0.35 inches, preferably approximately 0.18 inches. The length of the suture flange is generally between 0.2 and 1 inches, preferably approximately 0.5 inches. The angle at which the suture flange tapers to fit the distal end of the cannula is generally between 1 and 5 degrees, preferably approximately 3 degrees. The balloon occluder, when expanded, will generally have a diameter between 1 and 5 centimeters, preferably between about 2.5 and 4.0 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for purposes of clarity of understanding, been described in some detail by way of illustration and example, it will be obvious that certain changes and modifications may be practiced which will still fall within the scope of the appended claims.

What is claimed is:

1. A method for minimally invasive aortic cannulation, comprising the steps of:

providing a cannula having a proximal end, a distal end, and a lumen therebetween, the cannula having an expandable occluder mounted on the distal end;

providing an elongate member having proximal and distal ends, an actuating mechanism mounted at the proximal end of the elongate member, and a surgical blade mounted on the distal end of the elongate member and operable by manipulating the actuating mechanism at the proximal end;

inserting the elongate member into the lumen of the cannula;

making an incision on the aorta by activating the surgical blade on the elongate member;

inserting the cannula through the incision;

advancing the distal end of the cannula into the aorta;

withdrawing the elongate member from the lumen of the cannula; and expanding the occluder to isolate the heart and coronary blood vessels from the peripheral vascular system.

2. The method of claim 1, wherein the occluder further comprises a balloon occluder.

3. The method of claim 2, further comprising the step of delivering oxygenated blood through the lumen of the cannula to the aorta.

4. The method of claim 1, wherein the proximal end of the cannula is adapted for attachment to a bypass oxygenator machine.

5. The method of claim 1, further comprising the step of performing cardiopulmonary bypass.

6. The method of claim 1, further comprising the step of performing coronary artery bypass grafting surgery.

7. The method of claim 1, further comprising the step of performing heart valve repair.

* * * * *